United States Patent
Hassan et al.

(10) Patent No.: US 7,592,493 B2
(45) Date of Patent: Sep. 22, 2009

(54) HIGH SHEAR PROCESS FOR CYCLOHEXANOL PRODUCTION

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

(*) Notice: Subject to any disclaimer, the term of this patent is extended or adjusted under 35 U.S.C. 154(b) by 0 days.

(21) Appl. No.: 12/138,279

(22) Filed: Jun. 12, 2008

(65) Prior Publication Data
US 2009/0005608 A1    Jan. 1, 2009

Related U.S. Application Data

(60) Provisional application No. 60/946,584, filed on Jun. 27, 2007.

(51) Int. Cl.
    *C07C 35/08* (2006.01)
(52) U.S. Cl. .................................................. 568/836
(58) Field of Classification Search ............... 568/836
    See application file for complete search history.

(56) References Cited

U.S. PATENT DOCUMENTS 5,892,122 A    4/1999  Ostermaier et al.

FOREIGN PATENT DOCUMENTS

| JP | 09202742 A | 8/1997 |
| JP | 15261484 A | 9/2003 |
| RU | 2 293 075 C2 * | 10/2007 |
| WO | 0003963 A | 1/2000 |

* cited by examiner

*Primary Examiner*—Porfirio Nazario Gonzalez
(74) *Attorney, Agent, or Firm*—Conley Rose, P.C.

(57) ABSTRACT

Use of a high shear mechanical device incorporated into a process for the production of cyclohexanol is capable of decreasing mass transfer limitations, thereby enhancing the cyclohexanol production process. A system for the production of cyclohexanol from air oxidation of cyclohexane, the system comprising a high shear device, the outlet of the high shear device fluidly connected to the inlet of a reactor; the high shear device capable of providing a dispersion of air bubbles within a liquid comprising cyclohexane, the bubbles having an average bubble diameter of less than about 100 μm.

13 Claims, 2 Drawing Sheets

HIGH SHEAR PROCESS FOR CYCLOHEXANOL PRODUCTION

CROSS-REFERENCE TO RELATED APPLICATIONS

This application claims the benefit under 35 U.S.C. § 119 (e) of U.S. Provisional Patent Application No. 60/946,584 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of cyclohexanol, and more particularly to apparatus and methods for air oxidation of cyclohexane to produce cyclohexanol, in a high shear process. More specifically the disclosure relates to the reduction of mass transfer limitations in apparatus and methods for the air oxidation of cyclohexane to cyclohexanol.

2. Background of the Invention

Cyclohexanol is a saturated alicyclic alcohol; in its liquid state is a clear, oily, hygroscopic liquid. It is an intermediate chemical produced in combination with cyclohexanone by oxidizing cyclohexane. Cyclohexanol has applications in manufacturing soaps, detergents, cleaning fluids, and solvents. Cyclohexanol is used in the manufacture of certain raw materials, such as adipic acid, for the production of nylon.

Cyclohexanol and cylohexanone are oxidized during the production of adipic acid. A mixture of cyclohexanol and cyclohexanone may be referred to as ketone-alcohol oil, or KA oil. Cyclohexanol comprises the alcohol portion (A); cyclohexanone comprises the ketone (K) portion of the mixture. Industrially, the production of a cyclohexanol and cyclohexanone mixture is more economically favorable than to produce either individual component separately. Liquid-phase oxidation of cyclohexane may be shifted away from cyclohexanol and toward cyclohexanone, via the use of catalyst, for example, $TiO_2$.

Accordingly, there is a need in the industry for improved processes for the production of cyclohexanol whereby the mixing of cyclohexane and air are increased, so that production of cyclohexanol is more commercially feasible.

SUMMARY OF THE INVENTION

A high shear system and method for accelerating air oxidation of cyclohexane is disclosed. The disclosed high shear method makes possible a reduction in mass transfer limitations, thereby improving reaction conditions in the reactor such as the reaction rate, temperature, pressure, time and/or product yield. In accordance with certain embodiments of the present disclosure, a method is provided that makes possible an increase in the rate of acetic anhydride production by providing for more optimal time, temperature and pressure conditions than are conventionally used.

The process employs a high shear mechanical device to provide enhanced time, temperature and pressure conditions resulting in accelerated chemical reactions between multi-phase reactants.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
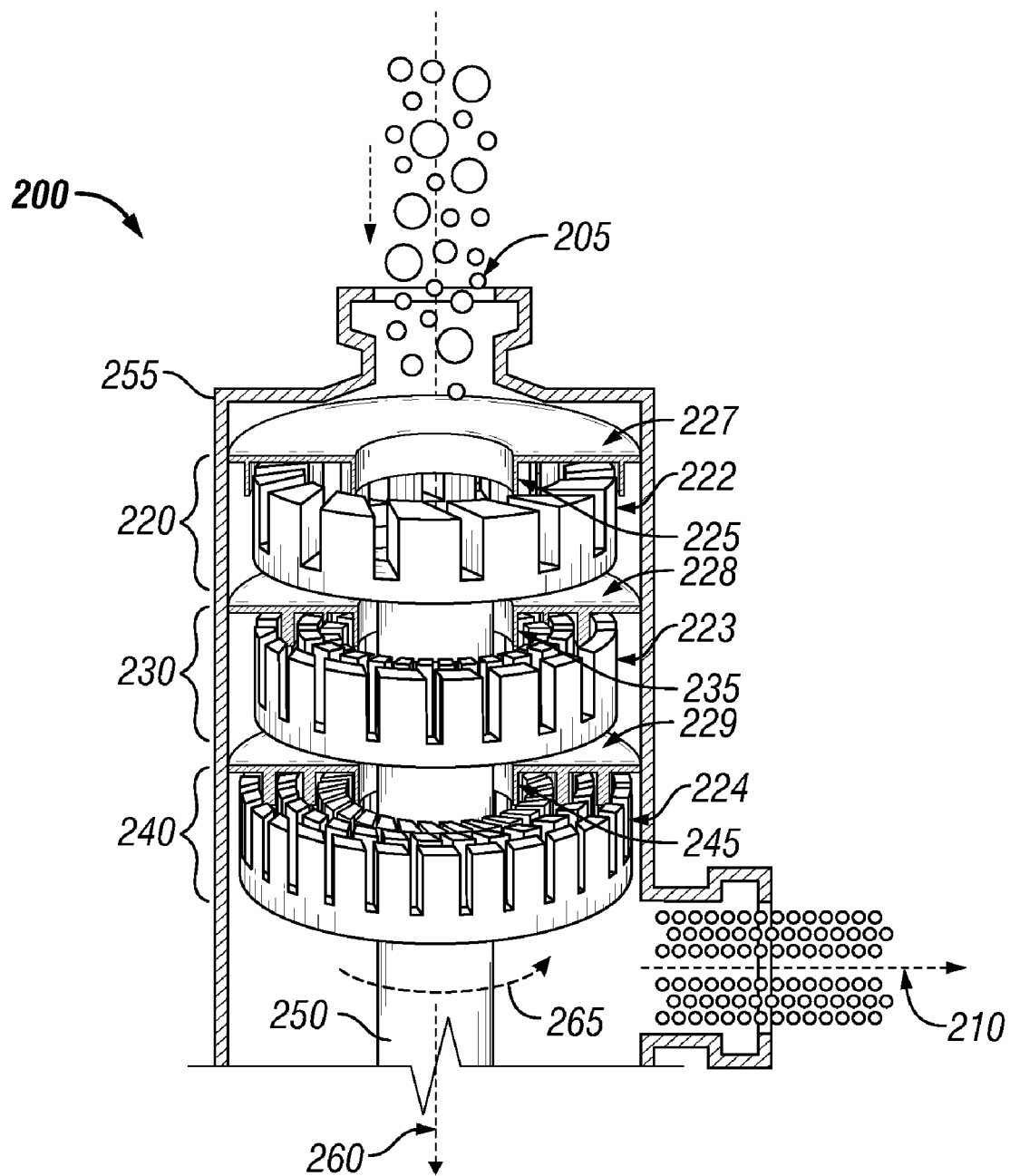
FIG. 1 is a FIG. 1 is a cross-sectional diagram of a high shear device for the production of cyclohexanol.

A system and method employs an external high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there may be the additional rate limiting factor of having the reaction products removed from the surface of the catalyst to enable the catalyst to catalyze further reactants.

In conventional reactors, contact time for the reactants and/or catalyst is often controlled by mixing which provides contact between two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 μm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and may yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, may achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $= \pi \cdot D \cdot n$, where V is the tip speed, D is the diameter of the rotor, in meters, and n is the rotational speed of the rotor, in revolutions per second. Tip speed is thus a function of the rotor diameter and the rotation rate.

For colloid mills, typical tip speeds are in excess of 23 m/sec (4500 ft/min) and may exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/l/min) may be made by measuring the motor energy (kW) and fluid output (l/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor. The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, tip speeds, output rpm, and flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," Current Science 91 (No. 1): 35-46 (2006). The high shear mixing device of certain embodiments of the present system and methods is operated under what are believed to be cavitation conditions effective to dissociate the cyclohexane into free radicals exposed to air for the formation of the cyclohexanol and cyclohexanone products.

Description of High Shear Process and System for Air Oxidation of Cyclohexane

Figure 2:
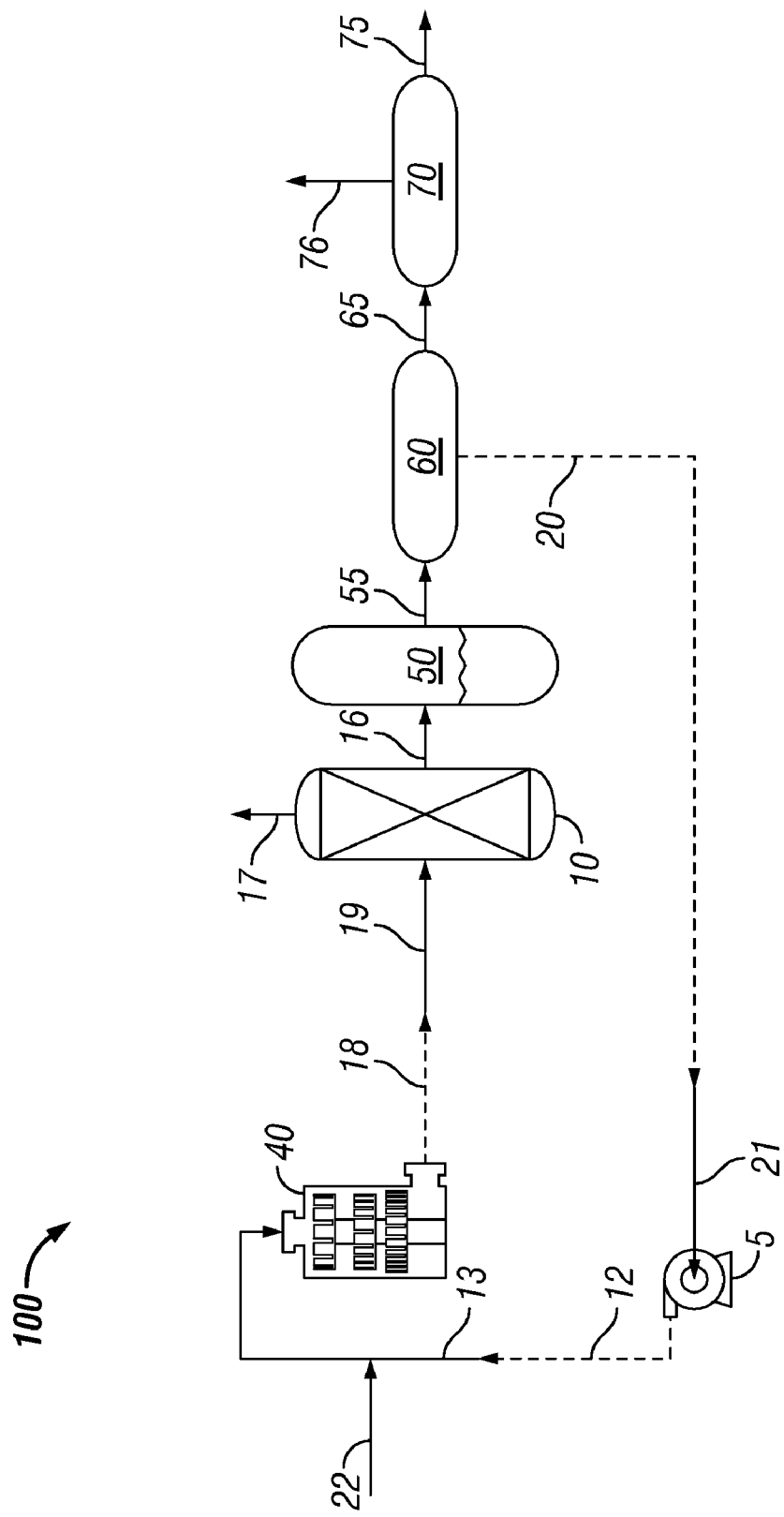
FIG. 2 is a process flow diagram of a system for the air oxidation of cyclohexane to produce cyclohexanol, including a high shear device, according to an embodiment of the present disclosure

High Shear System 100, hereinafter HSS 100, is suitable for the air oxidation of cyclohexane. FIG. 2 is a schematic of a flow diagram of a cyclohexane air oxidation process employing a multi-phase reaction system and comprising an external high shear mixer. As will be further discussed below, the disclosed mediator high shear process reduces resistance to mass and heat transfer between multiple phases during the oxidation reaction. Furthermore, as discussed below, air oxidation in the absence of an oxidation catalyst will be described, although it may be understood by one skilled in the art a catalyst may further be implemented to improve reaction conditions.

FIG. 2 illustrates the basic components of a representative high shear system 100 comprising pump 5, high shear device 40, and reactor 10. High shear device 40 is positioned between pump 5 and reactor 10. Pump 5 is used to provide a controlled flow throughout high shear device (HSD) 40 and high shear system 100 for cyclohexanol production. Pump inlet stream 21 comprises liquid cyclohexane for introduction to pump 5. Pump 5 increases the pressure of the pump inlet stream 21 to greater than about 203 kPa (about 2 atm); alternatively, the inlet stream 21 is pressurized to greater than about 304 kPa (about 3 atm). Additionally, pump 5 may build pressure throughout HSS 100. In this way, HSS 100 combines high shear with pressure to enhance reactant intimate mixing. Preferably, all contact parts of pump 5 are stainless steel, for example, 316 stainless steel. Pump 5 may be any suitable pump, for example, a Dayton Pressure Booster Pump Model 2P372E, Dayton Electric Co (Niles, Ill.).

The pressurized, liquid cyclohexane exits pump 5 via pump exit stream 12. Pump exit stream 12 is in fluid communication with HSD inlet stream 13. Further, HSD inlet stream 13 is in fluid communication with the HSD 40. In certain instances, dispersible gas stream 22 comprising an oxidant gas is introduced or injected to HSD inlet stream 13. In certain embodiments, the oxidant gas in dispersible gas stream 22 comprises air. Alternatively, the oxidant gas may be any gas known to one skilled in the art for oxidizing cyclohexane to cyclohexanol. In some embodiments the oxidant gas in dispersible gas stream 22 may continuously be fed into exit stream 12 to form HSD inlet stream 13. HSD inlet stream 13 comprises a mixture of oxidant gas and liquid cyclohexane. Dispersible gas stream 22 and pressurized pump exit stream 12 may be injected separately into HSD inlet stream 13 for processing by high shear device 40. In certain instances, HSD inlet stream 13 may undergo further processing or treating steps prior to introduction into HSD 40.

HSD 40 in fluid communication with HSD inlet stream 13. Alternatively, multiple high shear devices 40 are in fluid communication with HSD inlet stream 13. HSD 40 serves to intimately mix the cyclohexane solution in pump exit stream 12 with dispersible gas stream 22. As discussed in detail above, high shear device 40 is a mechanical device that utilizes, for example, a stator rotor mixing head with a fixed gap between the stator and rotor. In high shear device 40, the oxidant gas and cyclohexane are mixed to form an emulsion comprising microbubbles and nanobubbles of the oxidant gas. In embodiments, the resultant dispersion comprises bubbles in the submicron size. In embodiments, the resultant dispersion has an average bubble size less than about 1.5 µm. In embodiments, the mean bubble size is less than from about 0.1 µm to about 1.5 µm. Not to be limited by a specific method, it is known in emulsion chemistry that submicron particles dispersed in a liquid undergo movement primarily through Brownian motion effects. Thus it is believed that submicron gas particles created by the high shear device 40 have greater mobility through boundary layers of solid catalyst particles thereby facilitating and accelerating the catalytic reaction through greater transport of reactants. In embodiments, the high shear mixing produces gas bubbles capable of remaining dispersed at atmospheric pressure for about 15 minutes or longer depending on the bubble size. In embodiments, the mean bubble size is less than about 400 nm; more preferably, less than about 100 nm. HSD 40 serves to create an emulsion of oxidant gas bubbles within high shear inlet stream 13 comprising cyclohexane and air. The emulsion may further comprise a micro-foam.

In certain embodiments, the formation of an air and cyclohexane emulsion initiates the air oxidation reactions that form cyclohexanol. Air oxidation reactions may occur whenever suitable time, temperature, and pressure conditions exist. In this sense air oxidation could occur at any point in the flow diagram of FIG. 2 if temperature and pressure conditions are suitable. In certain embodiments comprising a slurry based catalyst, reaction is more likely to occur at points outside reactor 10 shown in FIG. 2. In such embodiments, a discrete reactor is often desirable to allow for increased residence time, agitation and heating and/or cooling. In embodiments wherein a fixed bed catalyst is utilized, the presence of catalyst in the emulsion will affect the rate of air oxidation.

The emulsion exits HSD 40 via HSD exit stream 18. High shear device exit stream 18 fluidly couples HSD 40 and reactor 10. Further, the emulsion exits HSD 40 via HSD exit stream 18. HSD exit stream 18 is in fluid communication with reactor inlet stream 19. Reactor inlet stream 19 couples HSD inlet stream 18 and reactor 10. In certain embodiments, HSD exit stream 18, and reactor inlet stream 19 are analogous; and in further instances, HSD exit stream 18 comprises reactor inlet stream 19. Alternatively, reactor inlet stream 19 may comprise HSD exit stream 18 which optionally has undergone further processing prior to introduction to reactor 10.

In FIG. 2, the reactor 10 is any type of reactor in which the multiphase air oxidation reaction can propagate. The reactor 10 may be an oxidation tower reactor, a stirred tank rank, a static tank reactor, a stirred autoclave reactor, or a non-stirred autoclave reactor. Furthermore, reactor 10 may comprises a plurality of reactors, and in certain embodiments, reactor 10 may include a combination of different reactors. In certain embodiments, reactor 10 is configured as a semi-continuous, stirred, tank reactor.

Reactor 10 serves to contain the oxidant gas, comprising air, and the cyclohexane for the oxidation reaction to produce cyclohexanol. In embodiments, the temperature for air oxidation of cyclohexane is less than about 160° C., and preferably the temperature for air oxidation of cyclohexane is from about 80° C. to about 150° C. Additionally, heat exchangers may be used to maintain the reaction temperature in the reactor. Suitable locations for external heat transfer devices would be between the reactor 10 and the pump 5; between the pump 5 and the high shear mixer 40 or between the high shear mixer 40 and the reactor 10. There are many types of heat transfer devices that may be suitable and are known to those experienced in the art. Such exchangers might include shell and tube, plate, and coil heat exchangers. In embodiments, reactor 10 may primarily serve to cool fluid, as much of the reaction occurs in external high shear mixer 40 and throughout HSS 100. Furthermore, reactor 10 may comprise gas vent 17 for removing excess oxidant gas comprising air from HSS 100.

Reactor 10 is emptied by product stream 16. Product stream 16 comprising cyclohexanol, cyclohexanone, unconverted cyclohexane, cyclohexyl-hydroperoxide (CHHP), and any other byproducts may be further processed to isolate cyclohexanol or cyclohexanone. Upon removal from reactor 10, product stream 16 comprising cyclohexanol may be passed to product recovery systems downstream of reactor 10 for further processing as known to those of skill in the art.

For example, product stream 16 may be in fluid communication with a ketone-alcohol (KA) distillation system 99. The KA oil distillation system comprises thermal treatment vessel 50 and a plurality of distillation columns 60, 70. In certain instances CHHP may be decomposed to produce additional cyclohexanone (ketone, K) and cyclohexanol (alcohol, A) by KA distillation system 99.

In embodiments, decomposition vessel 50 is configured for the decomposition of CHHP. The product stream 55 from decomposition vessel 50 is in fluid communication with at least distillation column 60. In certain embodiments, there is a plurality of distillation columns 60. Distillation column(s) 60 are configured to separate unreacted cyclohexane stream 20 for recycling to pump inlet stream 21. Distillation column (s) 60 produce distillate stream 65, comprising cyclohexanol, and/or cyclohexanone. In certain embodiments, distillate stream 65 comprises crude ketone-alcohol (KA). Furthermore distillate 65 from distillation column(s) 60 is fluidly coupled to second distillation column(s) 70. Second distillation column(s) 70 further refine distillate 65 to produce refined KA stream 76 and non volatile tails stream 75.

In KA oil distillation system 99, product stream 16 undergoes thermal decomposition of CHHP 50 to produce more of desirable products as described herein, in the decomposition vessel 50. Decomposition of CHHP may be performed, for example, via thermal decomposition, catalytic decomposition, catalytic hydrogenation, or other catalytic methods, such as the use of gold catalyst and the like. Thermal decomposition may be performed at temperatures of from about 120° C. to about 175° C. CHHP hydrogenation is carried out with heterogeneous catalysts, at temperatures between about 100° C. to about 160° C. Hydrogenation catalysts include but not limited to palladium on silica or alumina support. In embodiments, CHHP decomposition is accomplished without hydrogen via the use of different heterogeneous catalysts such as gold deposited on silica or alumina at temperatures between about 100° C. and about 160° C. In embodiments, CHHP decomposition is accomplished by metal catalyzed decomposition in caustic aqueous solution. This may be achieved by contacting the CHHP with cobalt, chromium, or a mixture thereof, in caustic solutions, preferably sodium hydroxide. When using either, or both, of these metals for CHHP decomposition the concentration of Co and/or Cr may be between 0.1 and 20 ppm. In embodiments, decomposition vessel 50 is configured to maintain a temperature of at least 100° C.

Product stream 55, from decomposition vessel 50, is in fluid communication with distillation column(s) 60. Distillation column(s) 60 are configured such that the unconverted or, unreacted cyclohexane stream 20 may be distilled off and, in embodiments, recycled to pump inlet stream 21. The resulting distillate 65 comprising crude KA may be further refined in second distillation column(s) 70. In embodiments, second distillation column(s) 70 is operated at temperatures between from about 90° C. to about 170° C. Refined KA is distilled from second distillation column(s) 70 as stream 76, while nonvolatile residue tails stream 75 is collected from the bottom of second distillation column(s) 70 for other processes. In alternative instances, cyclohexane distillation and KA refining may be performed by different unit operations known to those of skill in the art, such as vacuum distillation, steam distillation, and the like, without limitation.

In embodiments, use of the disclosed process comprising reactant mixing by high shear device 40 allows use of lower temperature and/or pressure in reactor 10 than previously enabled. In embodiments, the high shear process provides a higher conversion of cyclohexane to cyclohexanol/cyclohexanone and/or decreased volumes of vent gas stream 17 due to more efficient air oxidation. In embodiments, the method comprises incorporating high shear device 40 into an established process thereby reducing the operating temperature and/or pressure of the reaction in external high shear reactor 40 and/or enabling the increase in production (greater throughput) compared to a process operated without high shear device 40. The process of the present invention should be conducted under conditions sufficient to promote the air oxidation of cyclohexane in the reactive mixture. It will be understood by those skilled in the art that conditions of temperature and pressure may vary depending on other variables such as the desired conversion, cyclohexane concentration, the heating/cooling efficiency of the reactor system, etc.

In embodiments, the method and system of this disclosure enable design of a smaller and/or less capital intensive process allowing selection of a reactor 10 having lower operating temperature and/or pressure capability than previously possible without the incorporation of external high shear mixer 40. In embodiments, the disclosed method reduces operating costs/increases production from an existing process. Alternatively, the disclosed method may reduce capital costs for the design of new processes. Potential benefits of this modified system include, but are not limited to, faster cycle times, increased throughput, reduced operating costs and/or reduced capital expense due to the possibility of designing smaller reactors and/or operating the reactor at lower temperature and/or pressure.

In embodiments, the process of the present disclosure provides for a residence time less than about ¾ the residence time for air oxidation of cyclohexane in the absence of external high shear mixing. In embodiments, the process of the present disclosure provides for a residence time of less than about ½ the residence time (for the same conversion) when compared to air oxidation of cyclohexane in the absence of external high shear mixing.

While preferred embodiments of the invention have been shown and described, modifications thereof may be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A method for producing cyclohexanol, the method comprising:
    forming a dispersion comprising liquid cyclohexane and oxidant gas utilizing a high shear device, wherein the dispersion comprises oxidant gas bubbles with a mean diameter of less than about 5 µm, and wherein the high shear device comprises at least one rotor and at least one stator;
    introducing the dispersion into a reactor from which a product comprising cyclohexanol is removed, wherein the operating temperature within the reactor is maintained at a temperature of less than about 160° C.

2. The method of claim 1 further comprising pumping a liquid stream comprising cyclohexane to a pressure of at least about 203 kPa to produce a pressurized stream.

3. The method of claim 1 wherein the oxidant gas bubbles in the dispersion have an average diameter of less than about 1.5 µm.

4. The method of claim 1 wherein forming the dispersion comprises rotating the at least one rotor at a tip speed of at least 5 m/s.

5. The method of claim 1 wherein forming the dispersion comprises rotating the at least one rotor at a tip speed of at least about 20 m/s.

6. The method of claim 4 wherein forming the dispersion comprises producing a localized pressure of about 1000 MPa at the tip of the at least one rotor.

7. The method of claim 1 wherein forming the dispersion comprises subjecting the oxidant gas and liquid cyclohexane to a shear rate of greater than about $20,000 s^{-1}$.

8. The method of claim 1 wherein forming the dispersion comprises an energy expenditure of at least 1000 W/m$^3$.

9. The method of claim 1 wherein the dispersion comprises a micro-foam.

10. The method of claim 1 further comprising treating the product by distillation.

11. The method of claim 1 wherein the oxidant gas comprises air.

12. A method for producing cyclohexanol, the method comprising:

forming a dispersion of oxidant gas bubbles in solution comprising cyclohexane by introducing liquid cyclohexane and oxidant gas into a high shear device and subjecting the mixture of liquid cyclohexane and oxidant gas to a shear rate of at least 20,000s$^{-1}$.

13. The method of claim 12 wherein the high shear device comprises at least one rotor and at least one stator.

* * * * *